(12) United States Patent
Hur et al.

(10) Patent No.: US 11,740,215 B2
(45) Date of Patent: Aug. 29, 2023

(54) GAS SENSOR DEVICES AND HOUSINGS

(71) Applicant: Honeywell International Inc., Charlotte, NC (US)

(72) Inventors: Sanghoon Hur, Seoul (KR); Changyoung Jung, Seoul (KR); Yosup Kim, Seoul (KR)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 158 days.

(21) Appl. No.: 17/478,007

(22) Filed: Sep. 17, 2021

(65) Prior Publication Data

US 2023/0087286 A1 Mar. 23, 2023

(51) Int. Cl.
*G01N 33/00* (2006.01)

(52) U.S. Cl.
CPC ................ *G01N 33/0009* (2013.01)

(58) Field of Classification Search
CPC ............ G01N 33/0009; G01N 33/1886
See application file for complete search history.

(56) References Cited

U.S. PATENT DOCUMENTS

| | | | |
|---|---|---|---|
| 3,839,902 A | 10/1974 | Scott | |
| 5,898,003 A | 4/1999 | DiSpirito et al. | |
| 11,573,173 B2 * | 2/2023 | Abramovich | G01N 30/64 |
| 2016/0187311 A1 | 6/2016 | Brooking et al. | |

FOREIGN PATENT DOCUMENTS

KR 1503688 B1 * 3/2015

OTHER PUBLICATIONS

English translation of KR101503688, accessed from iq.ip.com Apr. 13, 2023 (Year: 2015).*
European search report dated Jan. 20, 2023 for EP Application No. 22193495.

* cited by examiner

*Primary Examiner* — Kristina M Deherrera
*Assistant Examiner* — Jean F Morello
(74) *Attorney, Agent, or Firm* — Alston & Bird LIP

(57) ABSTRACT

Devices, assemblies, and associated methods are provided for gas sensors. An example device for use with a gas sensor includes a buoyant housing that receives the gas sensor therein, an inlet opening defined by the housing, a pump positioned within the housing, and an outlet opening. The pump is in fluid communication with the inlet opening and the gas sensor in an instance in which the gas sensor is received by the housing. The pump is configured to cause gas received by the inlet opening to be directed to the gas sensor for evaluation, and the outlet opening is configured to discharge gas exiting the gas sensor from the buoyant housing. In an operational condition in which the device is placed in a fluid, the buoyant housing is configured such that at least a portion of the buoyant housing floats above a surface of the fluid.

20 Claims, 9 Drawing Sheets

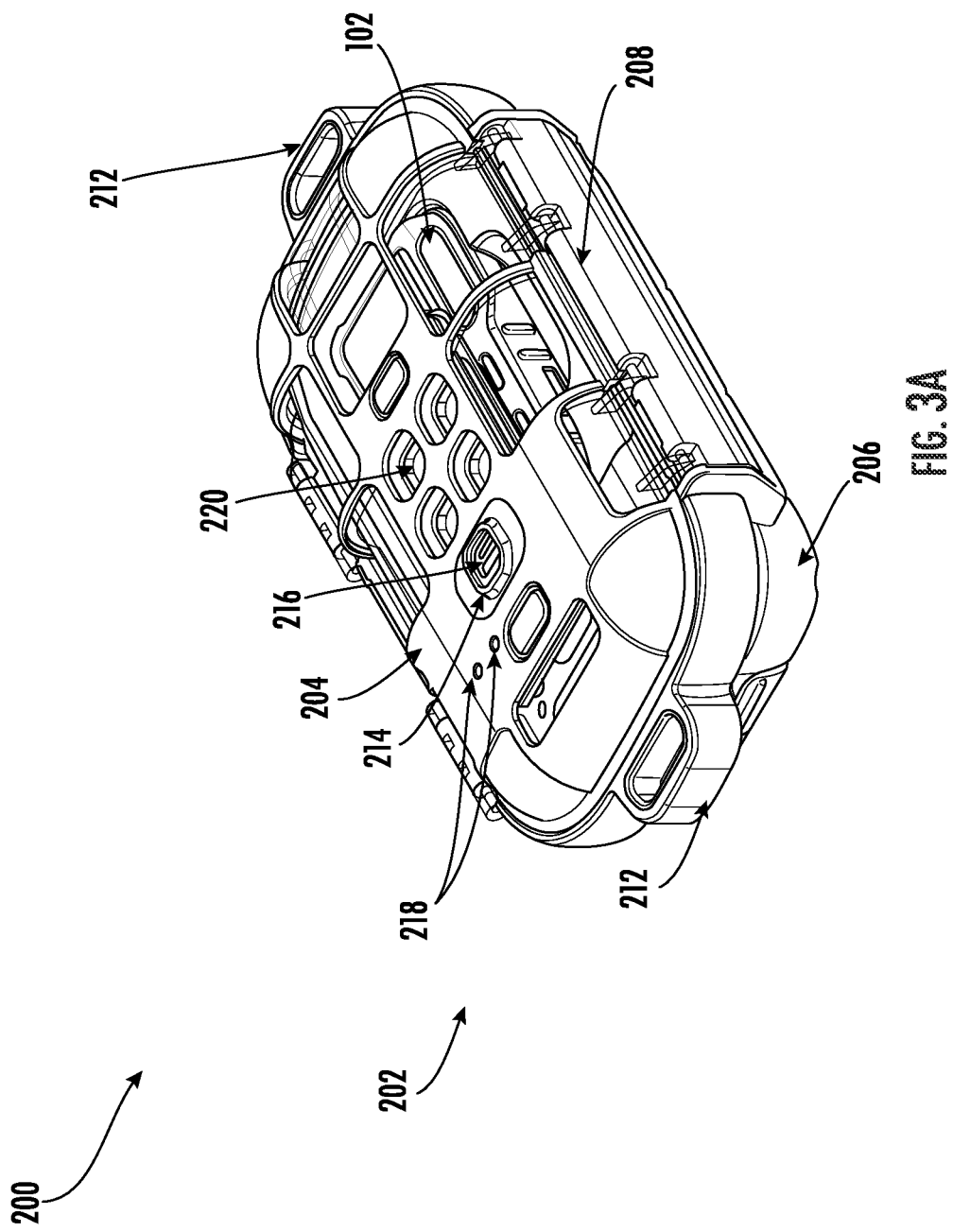

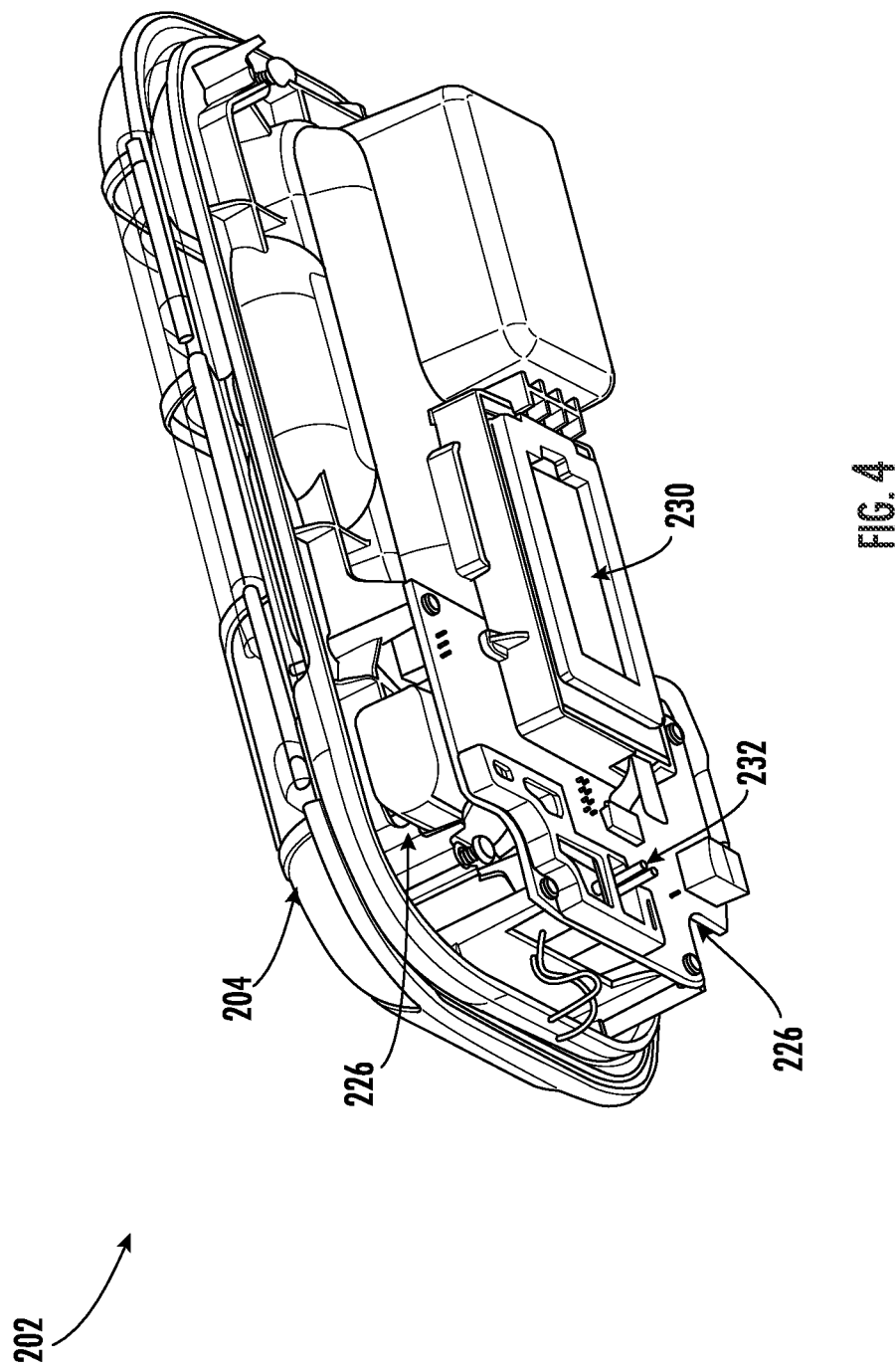

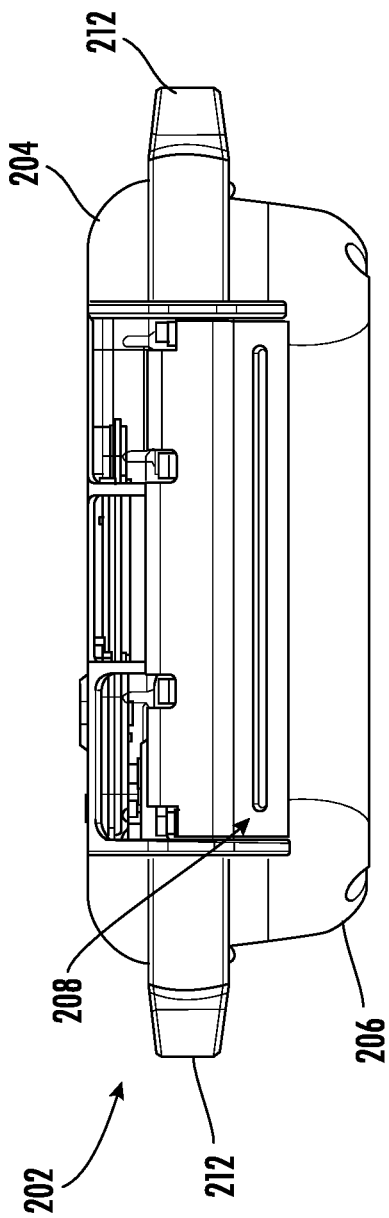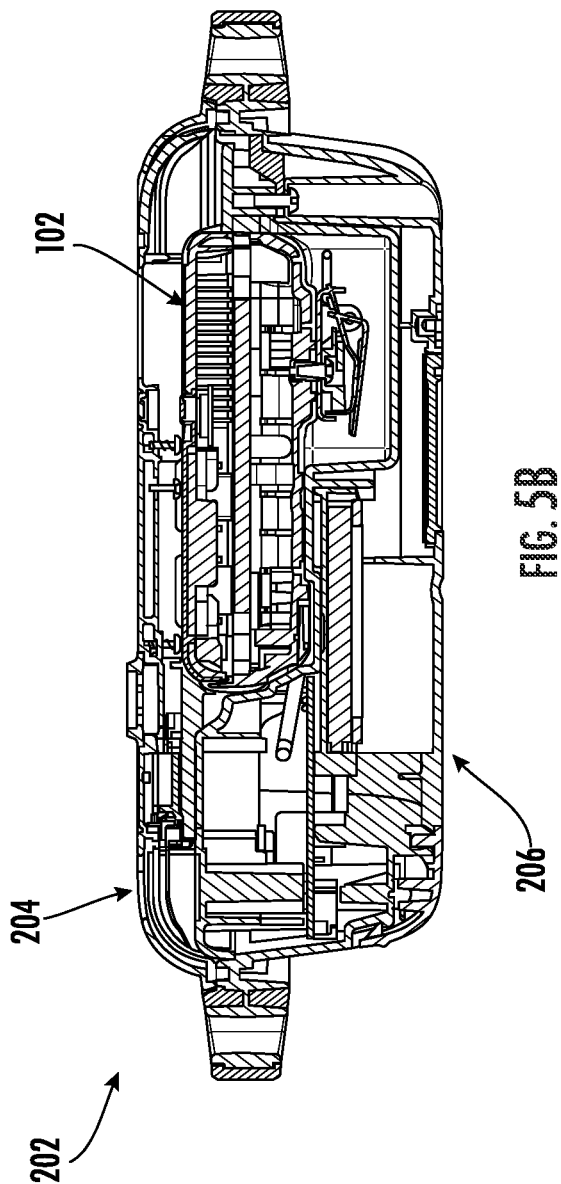

GAS SENSOR DEVICES AND HOUSINGS

TECHNOLOGICAL FIELD

Example embodiments of the present disclosure relate generally to gas sensors and, more particularly, to devices, systems, assemblies, and methods for providing a buoyant housing for gas sensors.

BACKGROUND

Gas sensors and detectors are used in a variety of industries, facilities, environments, etc. to detect the presence of various gasses and, in some cases, measure an amount or concentration of a particular gas. For example, gas sensors may be used to detect the presence or concentration of a particular gas within a tank, sewer line (e.g., down a manhole), or other environments in which a fluid may be present. However, the inventors have identified numerous deficiencies with these existing technologies in the field, the remedies for which are the subject of the embodiments described herein.

BRIEF SUMMARY

Apparatuses, devices, systems, assemblies, and associated methods of assembling/manufacturing are provided for gas sensors. An example device for use with a gas sensor may include a buoyant housing configured to receive the gas sensor therein and an inlet opening defined by the housing. The device may include a pump positioned within the housing, wherein the pump is in fluid communication with the inlet opening and the gas sensor in an instance in which the gas sensor is received by the housing. The pump may be configured to cause gas received by the inlet opening to be directed to the gas sensor for evaluation. The device may include an outlet opening defined by the housing that is configured to discharge gas exiting the gas sensor from the buoyant housing. In an operational condition in which the device is placed in a fluid, the buoyant housing may be configured such that at least a portion of the buoyant housing floats above a surface of the fluid.

In some embodiments, the buoyant housing may define a bottom cover and a top cover movably attached to the bottom cover. In such an embodiment, the top cover may be movable between a closed position in engagement with the bottom cover and an open position at which selective access to the interior of the buoyant housing is provided.

In some further embodiments, the bottom cover may define a cavity configured to support the gas sensor therein.

In some further embodiments, the top cover further may include a latch configured to, in the closed position, engage the bottom cover.

In some further embodiments, the inlet opening and the outlet opening may each be defined by the top cover.

In some further embodiments, the device may include one or more housing sealing membranes configured to, in the closed position, substantially seal the buoyant housing from the ingress of fluid such that the buoyant housing is substantially watertight.

In some further embodiments, the bottom cover further may define a pair of engagement elements configured to receive a strap attached thereto.

In some further embodiments, the top cover further may define one or more input features configured to receive an input from an operator of the device and actuate corresponding buttons of the gas sensor in an instance in which the gas sensor is received by the housing.

In other embodiments, the device may further include a gas block supported by the buoyant housing configured to direct gas between the inlet opening and the pump and between the pump and the gas sensor. In such an embodiment, the gas block may define a first channel extending between the inlet opening and the pump and a second channel extending between the pump and the gas sensor.

In any embodiment, the device may also include an outlet filter disposed on an inner surface of the top cover at the outlet opening.

In any embodiment, the device may also include an inlet filter defined by the top cover at the inlet opening.

In any embodiment, the device may also include a power source positioned within the housing and in electrical communication with at least the pump.

An example gas sensing assembly is also provided (e.g., a example device that includes the gas sensor). The assembly may include a gas sensor and a buoyant housing, wherein the gas sensor is positioned within the buoyant housing. The assembly may further include an inlet opening defined by the housing and a pump positioned within the housing. The pump may be in fluid communication with the inlet opening and the gas sensor. The pump may be configured to cause gas received by the inlet opening to be directed to the gas sensor for evaluation. The assembly may further include an outlet opening defined by the housing that may be configured to discharge gas exiting the gas sensor from the buoyant housing. In an operational condition in which the device is placed in a fluid, the buoyant housing may be configured such that at least a portion of the buoyant housing floats above a surface of the fluid.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings. The components illustrated in the figures may or may not be present in certain embodiments described herein. Some embodiments may include fewer (or more) components than those shown in the figures.

FIG. 3A is a perspective view of the example sensor device and assembly of FIG. 1 in a closed position according to an example embodiment;

FIG. 4 is a partial bottom view of a portion of the example sensor device and assembly of FIG. 1 according to an example embodiment;

FIG. 5A is a side view of the example gas sensor device and assembly of FIG. 3A according to an example embodiment;

FIG. 5B is a cross-sectional view of the side view of FIG. 5A according to an example embodiment;

DETAILED DESCRIPTION

Overview

Figure 1:
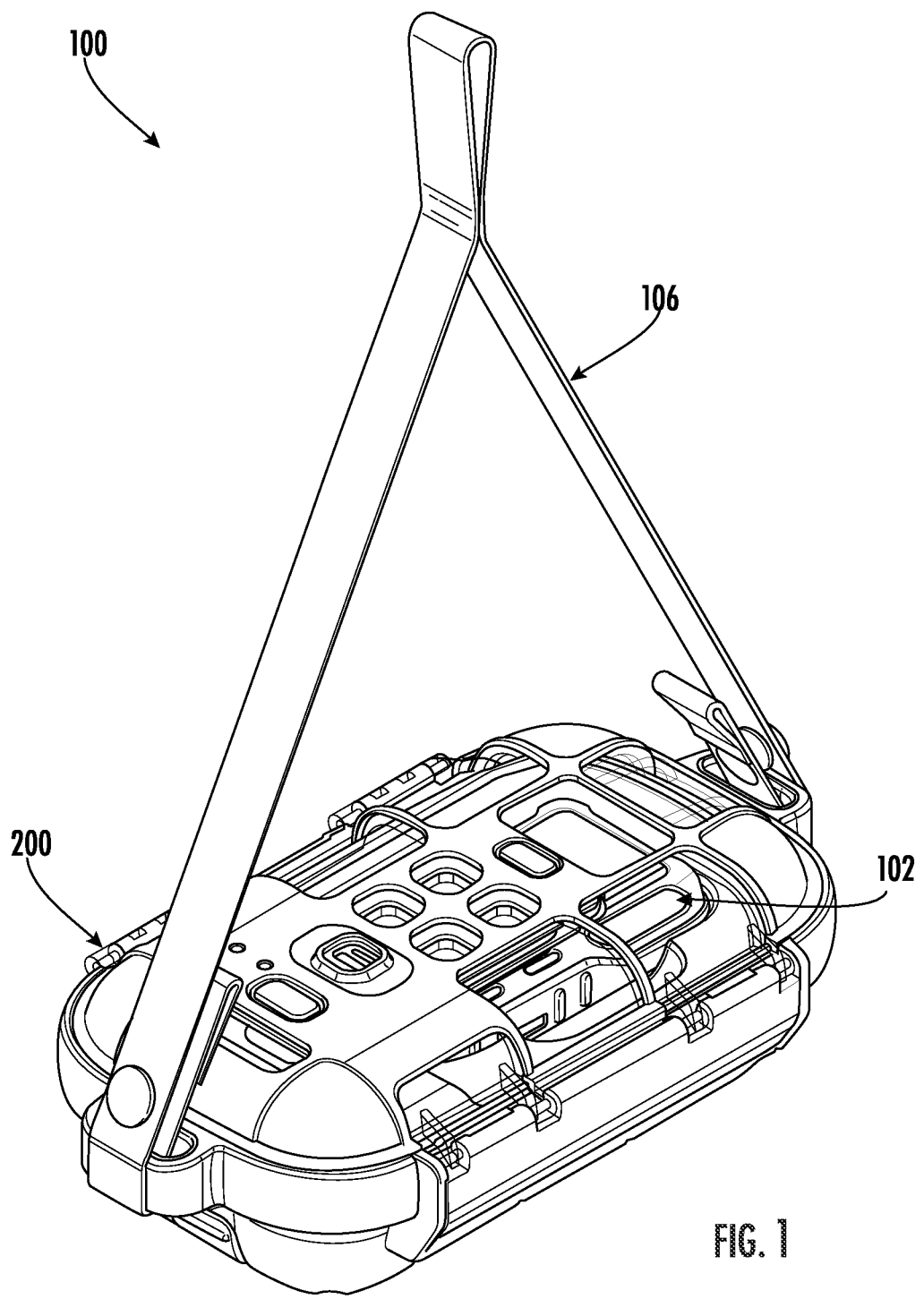
FIG. 1 is a perspective view of an example gas sensor device and assembly according to an example embodiment.

The present invention now will be described more fully hereinafter with reference to the accompanying drawings in which some but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used herein, terms such as "front," "rear," "top," etc. are used for explanatory purposes in the examples provided below to describe the relative position of certain components or portions of components. Furthermore, as would be evident to one of ordinary skill in the art in light of the present disclosure, the terms "substantially" and "approximately" indicate that the referenced element or associated description is accurate to within applicable engineering tolerances.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

As used herein, the phrases "in one embodiment," "according to one embodiment," "in some embodiments," and the like generally refer to the fact that the particular feature, structure, or characteristic following the phrase may be included in at least one embodiment of the present disclosure. Thus, the particular feature, structure, or characteristic may be included in more than one embodiment of the present disclosure such that these phrases do not necessarily refer to the same embodiment.

As used herein, the word "example" is used herein to mean "serving as an example, instance, or illustration." Any implementation described herein as "example" is not necessarily to be construed as preferred or advantageous over other implementations.

Gas Sensor Device and Assembly

As described above, gas sensors and detectors are used in a variety of industries, facilities, environments, etc. to detect the presence of various gasses and, in some cases, measure an amount or concentration of a particular gas. Often, gas detectors are employed to detect gases that are toxic, explosive, or otherwise dangerous (e.g., when present and/or when present at sufficient concentrations). In some implementations, these gas sensors or detectors may be deployed into manufacturing facilities to alarm workers of potentially dangerous conditions and/or may be installed in homes to do the same. In other instances, gas sensors may be used to detect the presence or concentration of a particular gas within a tank, sewer line (e.g., down a manhole), or in other environments in which a fluid may be present. The presence of a fluid in these environments, however, poses a risk of damage to the gas sensor (e.g., shorting the electrical components of the gas sensor, corroding one or components, etc.). As such, conventional systems that use gas sensors around, near, or otherwise proximate fluids rely upon disparate systems in which a gas sensor is located remotely from the testing location.

By way of example, when operators are tasked with testing gasses within a large tank containing a fluid, with testing gasses within a sewer system (e.g., by entering a manhole or equivalent structure), or the like, a gas sensor is positioned outside of the tanker, sewer system, or the like. In these examples, a tube, hose, etc. is connected to the remotely located gas sensor and placed in the tanker, sewer system, etc. In these conventional systems, gas must travel from inside the testing location (e.g., within the sewer system, tanker, etc.) to the gas sensor, often over increased distances. This travel distance of the gas prior to testing may result in substantial delay in gas detection and/or concentration detection. Said differently, an operator located within a tank, sewer system, or the like may be in the presence of a hazardous gas, and the testing delay associated with conventional systems may result in an increased exposure time for the operator before an alarm is triggered. Accordingly, the embodiments of the present disclosure address these issues and others by providing a buoyant housing that receives the gas sensor therein so as to provide gas sensing that occurs proximate to an operator. As described hereafter, such a buoyant housing may employ various watertight inlets and outlets to receive and discharge, respectively, gas from within a testing location and may further leverage a pump within the buoyant housing to causing gas to be directed to the gas sensor for evaluation.

Figure 2C:
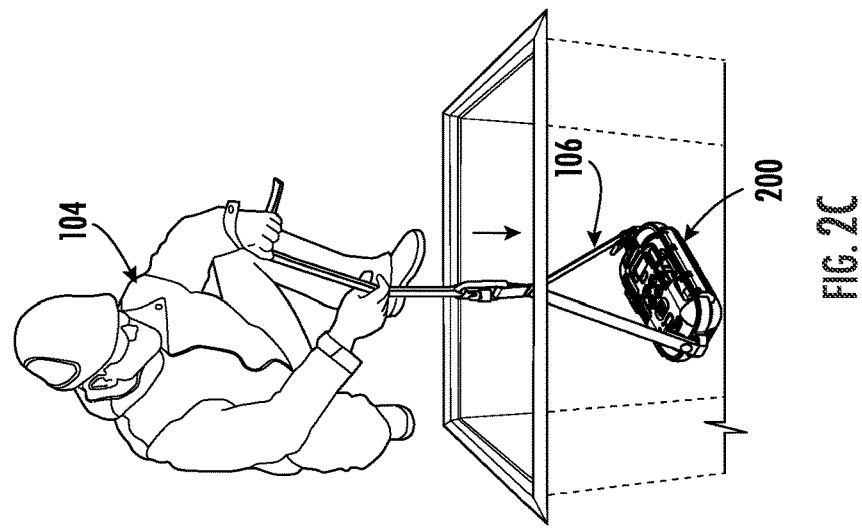
FIGS. 2A-2C illustrate the use of the example sensor device and assembly of FIG. 1.

With reference to FIG. 1, an example gas sensing assembly 100 of the present disclosure is illustrated. As shown, the assembly 100 may include a device for use with a gas sensor 200 (e.g., device 200) and a gas sensor 102 received therein. The assembly 100 may further include a strap 106 attached to the device 200 in order to, as shown in FIG. 2C, raise and/or lower the assembly 200 to a testing location. The embodiments of the present disclosure are hereafter described with reference to an example device 200 in that the device may be configured to receive a gas sensor 102 therein. Said differently, the device 200 may be used with a gas sensor 102 of any type, size, shape, or configuration such that, for example, the gas sensor 102 is removable from the device 200 (e.g., removable from the buoyant housing 202 as described hereafter). The present disclosure contemplates, however, that in some embodiments the gas sensor 102 may be included in the device 200 such that the embodiment refers to a gas sensing assembly 100 that includes the gas sensor 102. For example, the gas sensing assembly 100 may refer to embodiments in which the gas sensor 102 is secured within the device 200, formed as part of the device 200, and/or the like.

In any embodiment described herein, the gas sensor 102 may refer a device configured to receive (e.g., directly or indirectly) gas particles and evaluate the presence of particular types of gas (e.g., elements, molecules, etc.) and/or a particular concentration of a particular type of gas. As such, the gas sensor 102 may employ non-dispersive infrared (NDIR) techniques, semiconductor techniques, electrochemical techniques, and/or the like without limitation. Furthermore, the gas sensor 102 may be configured to detect the presence and/or concentration of any gas (e.g., $O_2$, CO, H$_2$S, SO$_2$, etc.) including any toxic gas, flammable gas, refrigerant gas, volatile organic material (VOC), or the like without limitation. By way of a non-limiting example, the gas sensor 102 may include or otherwise be operable with a Honeywell BW™ Icon, Honeywell BW™ Icon+, Honeywell BW™ Flex, Honeywell BW™ Ultra, Honeywell BW™ Solo, Honeywell MultiRAE, Honeywell AreaRAE, Honeywell ToxiRAE, and/or the like without limitation.

Figure 2B:
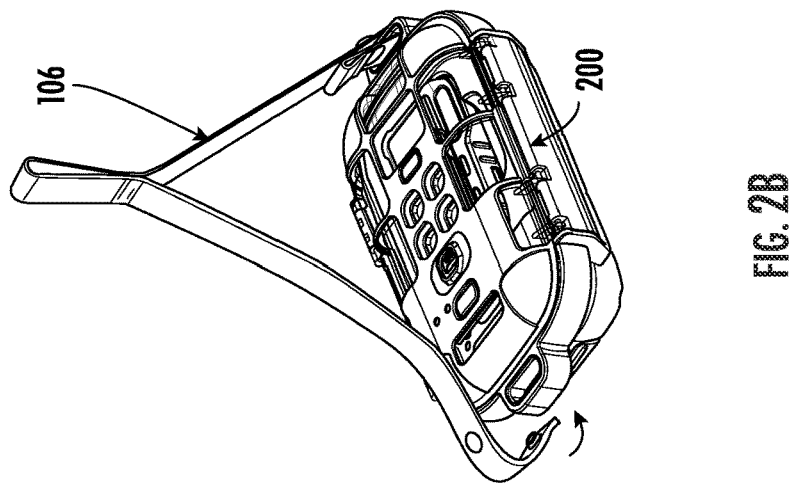
Figure 2A:
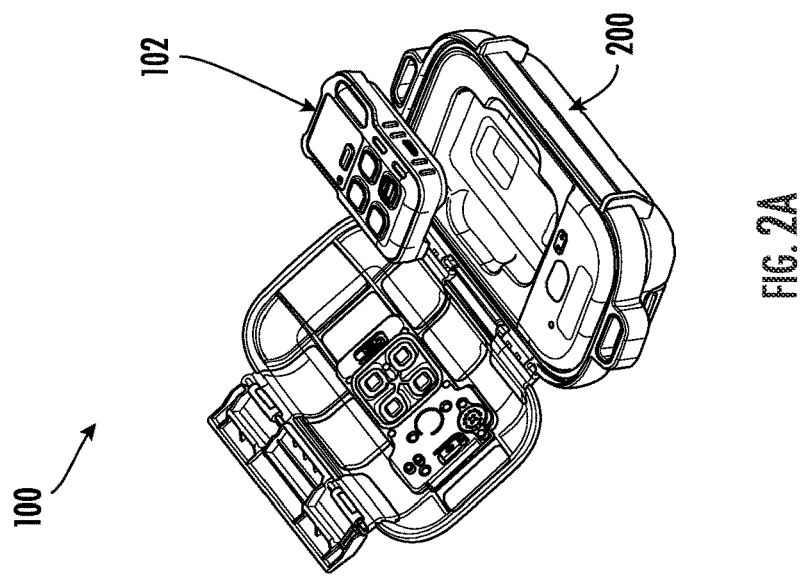
Figure 3B:
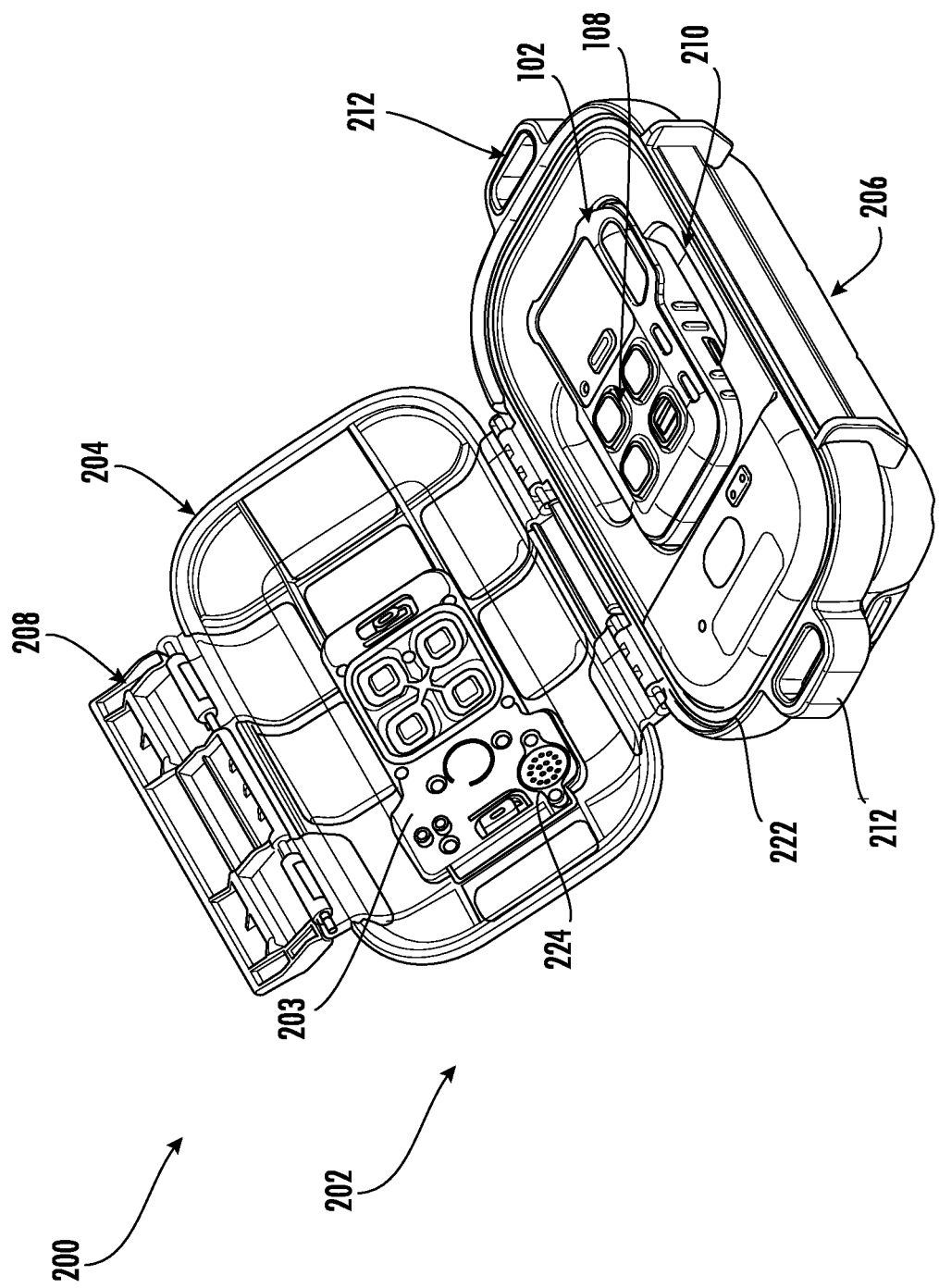
FIG. 3B is a perspective view of the example sensor device and assembly of FIG. 1 in an open position according to an example embodiment.

With reference to FIGS. 2A-2C, the gas sensing assembly 100 of FIG. 1 is illustrated in various stages of operation. The gas sensor 102 may be inserted within the device 200, as shown in FIG. 2A, and the gas sensor 102 may be enclosed by the device 200 as shown in FIG. 2B. As described hereafter, the device 200 may include a buoyant housing formed of a top cover and a bottom cover such that the gas sensor 102 may be enclosed within the buoyant housing by closing the top cover to engage the bottom cover. An operator (e.g., operator 104 in FIG. 2C) may attach a strap 106 to the device 200 so as to lower the assembly 100 (e.g., the device 200 in receipt of the gas sensor 102) into a testing location. Although described herein with reference to a strap 106, the present disclosure contemplates that any mechanism (e.g., rope, pulley, cable, cord, link, wire, linkage, etc.) may be attached to the assembly 100 so as to adjust the relative position of the assembly with respect to a testing location. As shown in FIGS. 3A-3B, described hereafter, the buoyant housing of the present disclosure (e.g., buoyant hosing 202) may define one or more engagement elements (e.g., engagement elements 212 in FIGS. 3A-3B) configured to engage the strap 106.

With reference to FIGS. 3A-3B, the device for user with a gas sensor 200 (e.g., device 200) is illustrated in a closed position and an open position, respectively. As shown, the device 200 may include a buoyant housing 202 that is formed of a top cover 204 and a bottom cover 206. The buoyant housing 202 may be configured to receive a gas sensor 102 therein as described above. As shown, the top cover 204 may be movably attached to the bottom cover 206 so as to move between a closed position as shown in FIG. 3A in which the gas sensor 102 is enclosed by the buoyant housing 202 and an open position as shown in FIG. 3B at which selective access to the interior of the buoyant housing 202 is provided. Said differently, the movable attachment between the top cover 204 and the bottom cover 206 may be such that an operator (e.g., operator 104 in FIG. 2C) may add or remove the gas sensor 102 from the buoyant housing 202. In an instance in which the gas sensor 102 is formed as part of the buoyant housing 202 (e.g., an integral implementation), the buoyant housing 202 may, for example, be fixed such that the housing is always in a closed position (e.g., removal of the gas sensor 102 is impossible or impracticable). In order to support the gas sensor 102 within the buoyant housing 202, the bottom cover 206 may, for example, define a cavity 210. Although described herein with reference to a cavity 210, the present disclosure contemplates that the buoyant housing 202 may define any feature (e.g., recess, opening, or the like) to support the gas sensor 102. Furthermore, the cavity 210 may be dimensioned (e.g., sized and shaped) based upon the corresponding dimensions of the gas sensor 102.

In order to secure the buoyant housing 202 in the closed position, the top cover 204 may define a latch 208 configured to engage the bottom cover 206. As shown, the latch 208 may be pivotally attached to the top cover 204 such that the latch 208 may move from a position in engagement with a corresponding feature of the bottom cover 206 to a disengaged position at which the buoyant housing 202 may be opened. As described above, the use of gas sensors 102 in environments in which a fluid may be present (e.g., a tank, sewer line (e.g., down a manhole), etc.) poses a risk of damage to the gas sensor 102 (e.g., shorting the electrical components of the gas sensor, corroding one or components, etc.). As such, the device 200 may further include one or more housing sealing membranes 222 configured to, in the closed position, substantially seal the buoyant housing 202 from the ingress of fluid such that the buoyant housing 202 is substantially watertight. For example, the sealing membrane 222 may be positioned along a peripheral edge of the bottom cover 206 and/or the top cover 204 so as to seal the contact between the covers 204, 206. The present disclosure contemplates that the buoyant housing 202 may leverage any mechanism for sealing the connection between the top cover 204 and the bottom cover 206 and may, in some embodiments, comply with applicable ingress protection (IP) ratings. By way of a particular, non-limiting example, the buoyant housing may be sealed so as to comply with IP7 or IP8 ratings.

In order for the device 200 of the present disclosure to operate proximate a testing location that may include a fluid, the buoyant housing 202 may be configured (e.g., dimensioned, shaped, etc.) such that at least a portion of the buoyant housing 202 floats above a surface of the fluid. In other words, in an operational condition (e.g., configuration, position, etc.) in which the device 200 is placed in a fluid, the buoyant housing 202 may be configured such that at least a portion of the buoyant housing 202 floats above a surface of the fluid such that operation of the gas sensor 102 therein may occur as described hereafter. Buoyancy refers to the upward force exerted on an object by a fluid in opposition to the weight of the object (e.g., the force of gravity acting on the object). As such, for an object to float in a fluid, the buoyant force exerted on the object by the fluid must balance the object's weight. Archimedes' principle further holds that the buoyant force equals the weight of the fluid displaced by the object. The present disclosure therefore contemplates that the buoyant housing 202 may be dimensioned (e.g., sized and shaped) in accordance with Archimedes' principle in that the fluid displaced by the buoyant housing 202 (e.g., accounting for the density of said fluid) may be such that at least a portion buoyant housing 202 floats above a surface of the fluid. In some embodiments, the buoyant housing 202 may be dimensioned (e.g., sized and shaped) such that the bottom cover 206 is substantially submerged when placed in a fluid but the top cover 204 floats above the surface of the fluid. In doing so, the buoyant housing 202 may allow an operator to access one or more features of the device 200 while in the operational condition (e.g., placed in a fluid).

With continued reference to FIGS. 3A-3B, the device 200 may further include an inlet opening 214 defined by the buoyant housing 202 and an outlet opening 218 defined by the buoyant housing 202. As shown, in some embodiments, the top cover 204 may define the inlet and outlet opening(s) 214, 218. For example, in the operational condition in which the device 200 is placed in a fluid as described above, the inlet opening 214 and/or the outlet opening 218 may be located such that air may enter or exit, respectively, these openings 214, 218. In other words, the inlet opening 214 and/or the outlet opening 218 may be positioned to avoid the ingress of fluid when the device 200 is placed in a fluid.

The inlet opening 214 may be configured to receive a flow of gas into the device 200, such as from a hose or other conduit connected thereto. For example, a hose (not shown) connected to the inlet opening may be positioned by the operator within the testing location so as to test the gas at particular locations selected by the operator. In other embodiments, the inlet opening 214 may be configured to passively receive gas therein from the testing environment, such as due to pressure from the pump described hereafter. The inlet opening 214 may further be associated with an inlet filter 216 defined by the top cover 204 at the inlet opening 214. The inlet filter 216 may, for example, be configured to prevent the ingress of particulates, fluid, or any other element that may interfere with evaluation of the gas by the gas sensor 102. Although illustrated as a single inlet opening 214, the present disclosure contemplates that the top cover 204 may define any number of inlet openings 214 that are distinct (e.g., separate inlet openings and channels) or interconnected. Furthermore, the inlet opening 214 may be dimensioned (e.g., sized and shaped) based upon the intended application of the device 200, the particular gas sensor 102, and/or the like.

The outlet opening 218 may be configured to discharge (e.g., exhaust) gas exiting the gas sensor 102 from the buoyant housing 202. As described hereafter, following evaluation of the gas received by the inlet opening 214, gas may be output by the gas sensor 102 to, for example, the interior of the buoyant housing 202. In such an embodiment, the outlet opening 218 may be in fluid communication with the interior of the buoyant housing 202 so as to allow evaluated gas to exit the housing 202. The outlet opening 218 may further be associated with an outlet filter 224 disposed on an inner surface 203 of the top cover 204 at the outlet opening 218. Similar to the inlet filter 216, the outlet filet 224 may, for example, be configured to prevent the ingress of particulates, fluid, or any other element that may interfere with operation of the device 200. Although illustrated as a pair of outlet openings 218, the present disclosure contemplates that the top cover 204 may define any number of outlet openings 218 that are distinct (e.g., separate outlet openings and channels) or interconnected. Furthermore, the outlet opening(s) 218 may be dimensioned (e.g., sized and shaped) based upon the intended application of the device 200, the particular gas sensor 102, and/or the like.

As shown in FIG. 3A, the top cover 204 may further define one or more input features 220. These input features 220 may include one or more buttons, knobs, dials, etc. configured to receive an input from an operator (e.g., operator 104 in FIG. 2C) of the device 200. Such an input from the operator (e.g., a push of the button defined by the top cover 204) may, in some embodiments, actuate corresponding buttons 108 of the gas sensor 102 in an instance in which the gas sensor 102 is received by the housing 202. These input features 220 may allow the operator to, for example, select the type of gas for which the gas sensor 102 is testing, among any other function offered by the gas sensor 102.

With reference to FIG. 4, a partial bottom view of a portion of the example sensor device 200 is illustrated. As shown, the device 200 may further include a pump 226 that may be in fluid communication with the inlet opening 214 and the gas sensor 102. The pump may be configured to cause gas received by the inlet opening 214 to be directed to the gas sensor 102 for evaluation. The pump 226 may be positioned at any location within the buoyant housing 202 and may include a positive-displacement pump, impulse pump, velocity pump, gravity pump, steam pump, valveless pump, or any equivalent device configured to cause gas to enter the device 200 via the inlet opening 214 and cause said gas to flow to the gas sensor 102. In operation, as described hereafter with reference to FIGS. 6A-6D, the pump 226 may be configured to cause suction (e.g., induce negative pressure) to draw gas proximate the inlet opening 214 into the device 200 and may, via various fluidically coupled channels, direct this gas to the gas sensor 102 (e.g., to an inlet of the gas sensor 102). In order to supply power to at least the pump 226, the device 200 may include a battery 230 or equivalent power source. In some embodiments, the battery 230 may be configured to further supply power to the gas sensor 102. The device 200 may also include a printed circuit board (PCB) 228 configured to provide electrical connectivity between one or more elements of the device 200 and/or charging pins 228 to provide recharging of, for example, the battery 230 (e.g., when supplied with an external power source).

With reference to FIGS. 5A-5B, a side view and a cross-sectional view of the side view, respectively, are shown. As described above, the buoyant housing 202 may be dimensioned (e.g., sized and shaped) to not only accommodate gas sensors 102 of any type but also to ensure that at least a portion of the housing 202 floats above a surface of the fluid. The relative position between elements within the buoyant housing 202, however, may be adjusted based upon the intended application of the device 200. For example, in some embodiments, the gas sensor 102 may be formed integral to the buoyant housing 202 such that one or more components of the gas sensor 102 may be repositioned within the buoyant housing 202.

Figure 6C:
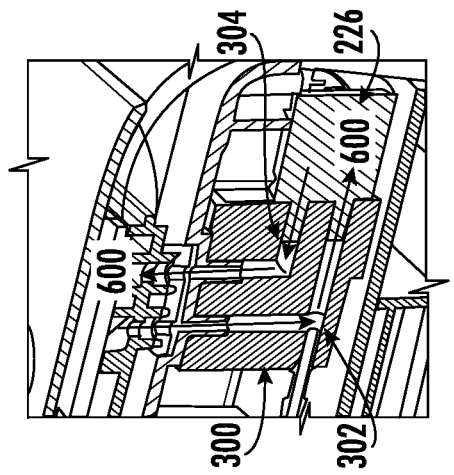
FIGS. 6A-6F illustrate an example gas flow through a sensor device and assembly of the present disclosure.
Figure 6B:
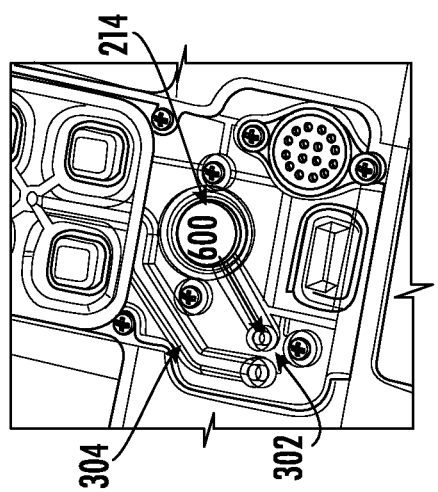
Figure 6A:
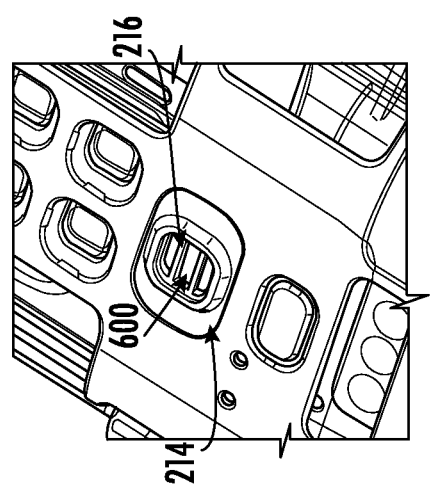
Figure 6F:
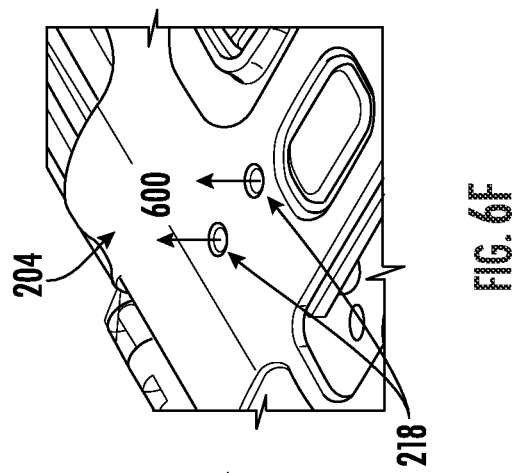

With reference to FIGS. 6A-6F, an example gas flow 600 through the device 200 is illustrated. As shown in FIG. 6A, the inlet opening 214 may be configured to receive a flow of gas into the device 200, such as from a hose, tube, or other conduit connected thereto. As described above, a hose (not shown) connected to the inlet opening 214 may be positioned by the operator within the testing location so as to test the gas at particular locations selected by the operator. The inlet filter 216 may further be configured to prevent the ingress of particulates, fluid, or any other element that may interfere with evaluation of the gas by the gas sensor 102. As noted above, the present disclosure contemplates that the top cover 204 may define any number of inlet openings 214 that are distinct (e.g., separate inlet openings and channels) or interconnected.

Figure 6E:
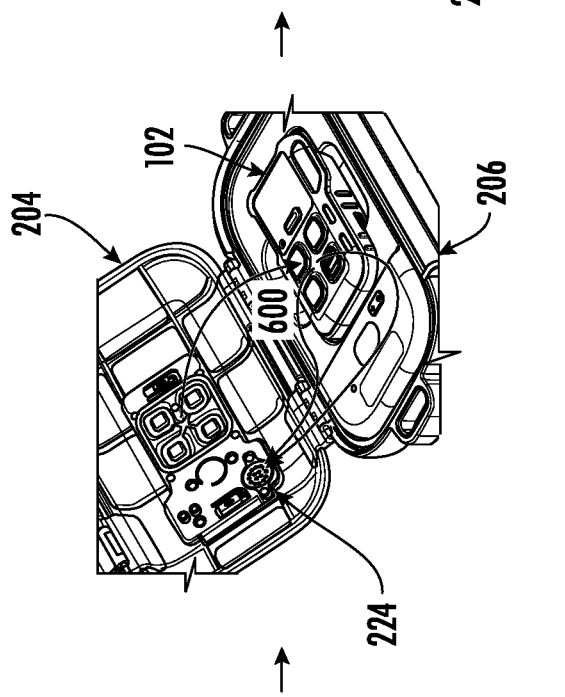
Figure 6D:
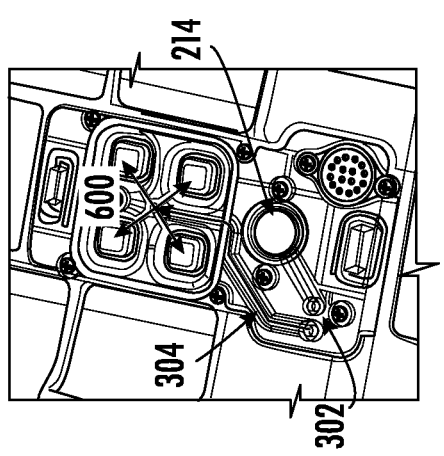

As shown in FIGS. 6B-6D, the device 200 may include a gas block 300 supported by the buoyant housing 202 and configured to direct the gas 600 between the inlet opening 214 and the pump 226 and between the pump 226 and the gas sensor 102. The gas block 300 may, for example, include a first channel 302 that extends between the inlet opening 214 and the pump 226 so as to provide fluid communication between the inlet opening 214 and the pump 226. As shown in FIGS. 6B and 6C, the first channel 302 may define a conduit, duct, groove, or any structure through which gas may flow. Furthermore, in some embodiments, a portion of the first channel 302 may extend substantially within a plane defined by the inlet opening 214 (e.g., substantially parallel with respect to a bottom, exterior surface of the bottom cover 206 and/or a top exterior surface of the top cover 204). The first channel 302 of the gas block 300 may further define a portion substantially perpendicular with respect to the plane defined by the inlet opening 214 that extends from the portion described above and terminates at a subsequent portion of the first channel 302. Said subsequent portion of the first channel 302 may be substantially parallel with respect to the plane defined by the inlet opening 214 and may be in line with the pump 226 (e.g., an inlet of the pump 226). Although described herein with various portions having respective positions and orientations, the present disclosure contemplates that the first channel 302 may include any number of channels (e.g., distinct or interconnected) in any position or orientation so as to direct the gas 600 from the inlet opening 214 to the pump 226.

The gas block 300 may further include a second channel 304 that extends between the pump 226 and the gas sensor 102. As shown in FIGS. 6C and 6D, the second channel 304 may define a conduit, duct, groove, or any structure through which gas may flow. Furthermore, in some embodiments, a portion of the second channel 304 may extend from an outlet of the pump and substantially parallel with respect to a plane defined by the inlet opening 214 (e.g., substantially parallel with respect to a bottom, exterior surface of the bottom cover 206 and/or a top exterior surface of the top cover 204). The second channel 304 of the gas block 300 may further define a portion substantially perpendicular with respect to the plane defined by the inlet opening 214 that extends from the portion described above and terminates at a subsequent portion of the second channel 302. Said subsequent portion of the second channel 304 may extend substantially within a plane defined by the inlet opening 214 and terminate at or proximate the gas sensor 102. For example, the second channel 304 may be in fluid communication with the gas sensor 102 by engaging with a corresponding inlet of the gas sensor 102. Although described herein with various portions having respective positions and orientations, the present disclosure contemplates that the second channel 304 may also include any number of channels (e.g., distinct or interconnected) in any position or orientation so as to direct the gas 600 from the pump 226 to the gas sensor 102.

As described above, the gas sensor 102 may be configured to receive gas particles (e.g., gas 600) from the second channel 304 of the gas block 300 and evaluate the presence of particular types of gas (e.g., elements, molecules, etc.) and/or a particular concentration of particular types of gas. Following the evaluation of the gas 600, the gas sensor 102 may output (e.g., emit, discharge, etc.) the gas 600 from the sensor into, for example, the interior of the buoyant housing 202. By way of example, the gas sensor 102 may define an outlet that is exposed to the interior of the buoyant housing 202 (e.g., in fluid communication with the interior of the buoyant housing 202) such that the gas 600 exits the gas sensor 102 and resides in the interior of the buoyant housing 202 as shown in FIG. 6E. As described above and as illustrated in FIG. 6F, the buoyant housing 202 may define an outlet opening 218 which may include one or more openings configured to discharge the gas 600 exiting the gas sensor 102 from the buoyant housing 202. As described above, the outlet opening 218 may further be associated with an outlet filter 224 that may be configured to prevent the ingress of particulates, fluid, or any other element that may interfere with operation of the device 200. Although illustrated as a pair of outlet openings 218, the present disclosure contemplates that the top cover 204 may define any number of outlet openings 218 that are distinct (e.g., separate outlet openings and channels) or interconnected.

Method of Assembling/Manufacturing

Figure 7:
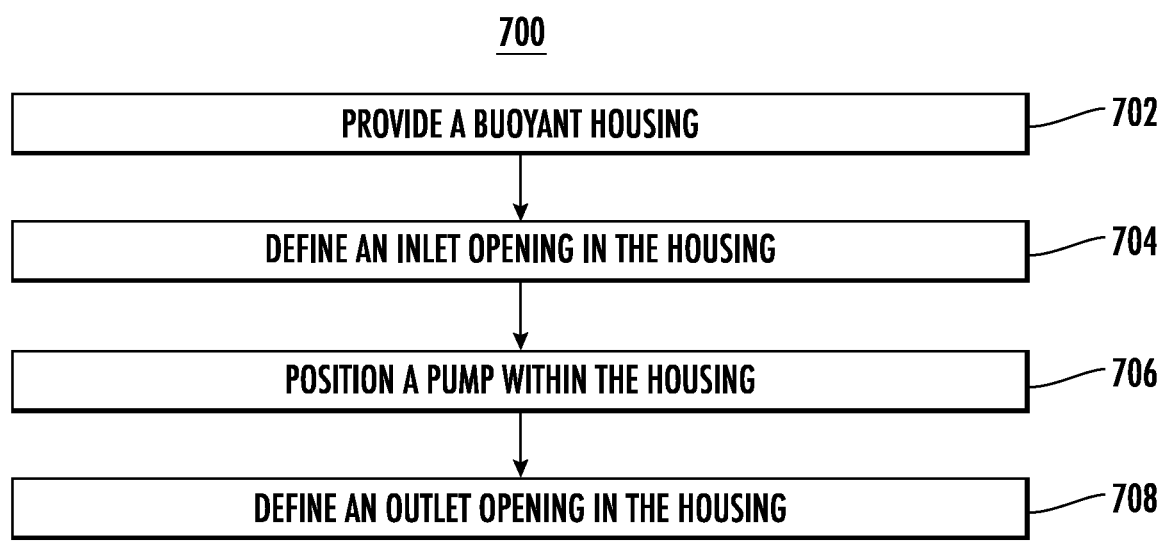
FIG. 7 illustrates an example method of assembling/manufacturing a sensor device and assembly of the present disclosure.

With reference to FIG. 7, an example method of assembling/manufacturing a device for use with a gas sensor (e.g., method 700) is illustrated. As shown in operation 702, the method 700 may include providing a buoyant housing. As described above, the buoyant housing may be formed of a top cover and a bottom cover and may be configured to receive a gas sensor therein as described above. The top cover may be movably attached to the bottom cover 206 so as to move between a closed position as shown in which the gas sensor is enclosed by the buoyant housing and an open position as shown at which selective access to the interior of the buoyant housing is provided. In order to support the gas sensor within the buoyant housing, the bottom cover may, for example, define a cavity. In order for the device of the present disclosure to operate proximate a testing location that may include a fluid, the buoyant housing may be configured (e.g., dimensioned, shaped, etc.) such that at least a portion of the buoyant housing floats above a surface of the fluid as detailed above. In other words, in an operational condition (e.g., configuration, position, etc.) in which the device is placed in a fluid, the buoyant housing may be configured such that at least a portion of the buoyant housing floats above a surface of the fluid such that operation of the gas sensor therein may occur as described above.

At operation 704, the method may include defining an inlet opening in the buoyant housing. As described above, the inlet opening may be configured to receive a flow of gas into the device, such as from a hose, tube, or other conduit connected thereto. A hose connected to the inlet opening may be positioned by the operator within the testing location so as to test the gas at particular locations selected by the operator. The inlet opening may be associated with an inlet filter that may further be configured to prevent the ingress of particulates, fluid, or any other element that may interfere with evaluation of the gas by the gas sensor.

At operation 706, the method 700 may include positioning a pump within the buoyant housing. As described above, the pump may be in fluid communication with the inlet opening and the gas sensor. The pump may be configured to cause gas received by the inlet opening to be directed to the gas sensor for evaluation. The pump may be positioned at any location within the buoyant housing and may include a positive-displacement pump, impulse pump, velocity pump, gravity pump, steam pump, valveless pump, or any equivalent device configured to cause gas to enter the device via the inlet opening and cause said gas to flow to the gas sensor. The pump may be configured to cause suction (e.g., induce negative pressure) to draw gas proximate the inlet opening into the device and may, via various fluidically coupled channel, direct this gas to the gas sensor (e.g., to an inlet of the gas sensor).

At operation 708, the method 700 may further include defining an outlet opening in the buoyant housing. As described above, following the evaluation of the gas, the gas sensor may output (e.g., emit, discharge, etc.) the gas from the sensor into, for example, the interior of the buoyant housing. The buoyant housing may therefore define an outlet opening which may include one or more openings configured to discharge the gas exiting the gas sensor from the buoyant housing. The outlet opening may further be associated with an outlet filter that may be configured to prevent the ingress of particulates, fluid, or any other element that may interfere with operation of the device. The present disclosure contemplates that the top cover may define any number of outlet openings that are distinct (e.g., separate outlet openings and channels) or interconnected.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A device for use with a gas sensor, the device comprising:
   a buoyant housing configured to receive the gas sensor therein;
   an inlet opening defined by the housing;
   a pump positioned within the housing, wherein the pump is in fluid communication with:
      the inlet opening; and
      the gas sensor in an instance in which the gas sensor is received by the housing, wherein the pump is configured to cause gas received by the inlet opening to be directed to the gas sensor for evaluation; and
   an outlet opening defined by the housing, wherein the outlet opening is configured to discharge gas exiting the gas sensor from the buoyant housing,
   wherein, in an operational condition in which the device is placed in a fluid, the buoyant housing is configured such that at least a portion of the buoyant housing floats above a surface of the fluid.

2. The device according to claim 1, wherein the buoyant housing defines a bottom cover and a top cover movably attached to the bottom cover, wherein the top cover is movable between a closed position in engagement with the bottom cover and an open position at which selective access to the interior of the buoyant housing is provided.

3. The device according to claim 2, wherein the bottom cover defines a cavity configured to support the gas sensor therein.

4. The device according to claim 2, wherein the top cover further comprises a latch configured to, in the closed position, engage the bottom cover.

5. The device according to claim 2, wherein the inlet opening and the outlet opening are each defined by the top cover.

6. The device according to claim 2, further comprising one or more housing sealing membranes configured to, in the closed position, substantially seal the buoyant housing from the ingress of fluid such that the buoyant housing is substantially watertight.

7. The device according to claim 2, wherein the bottom cover further defines a pair of engagement elements configured to receive a strap attached thereto.

8. The device according to claim 2, wherein the top cover further defines one or more input features configured to:
   receive an input from an operator of the device; and
   actuate corresponding buttons of the gas sensor in an instance in which the gas sensor is received by the housing.

9. The device according to claim 1, further comprising a gas block supported by the buoyant housing configured to direct gas between the inlet opening and the pump and between the pump and the gas sensor.

10. The device according to claim 9, wherein the gas block defines:
    a first channel extending between the inlet opening and the pump; and
    a second channel extending between the pump and the gas sensor.

11. The device according to claim 1, further comprising an outlet filter disposed on an inner surface of the top cover at the outlet opening.

12. The device according to claim 1, further comprising an inlet filter defined by the top cover at the inlet opening.

13. The device according to claim 1, further comprising a power source positioned within the housing and in electrical communication with at least the pump.

14. A gas sensing assembly comprising:
    a gas sensor;
    a buoyant housing, wherein the gas sensor is positioned within the buoyant housing;
    an inlet opening defined by the housing;
    a pump positioned within the housing, wherein the pump is in fluid communication with:
       the inlet opening; and
       the gas sensor, wherein the pump is configured to cause gas received by the inlet opening to be directed to the gas sensor for evaluation; and
    an outlet opening defined by the housing, wherein the outlet opening is configured to discharge gas exiting the gas sensor from the buoyant housing,
    wherein, in an operational condition in which the device is placed in a fluid, the buoyant housing is configured such that at least a portion of the buoyant housing floats above a surface of the fluid.

15. The assembly according to claim 14, wherein the buoyant housing defines a bottom cover and a top cover movably attached to the bottom cover, wherein the top cover is movable between a closed position in engagement with the bottom cover and an open position at which selective access to the interior of the buoyant housing is provided.

16. The assembly according to claim 15, wherein the inlet opening and the outlet opening are each defined by the top cover.

17. The assembly according to claim 15, further comprising one or more housing sealing membranes configured to, in the closed position, substantially seal the buoyant housing from the ingress of fluid such that the buoyant housing is substantially watertight.

18. The assembly according to claim 15, wherein the top cover further defines one or more input features configured to:
    receive an input from an operator of the device; and
    actuate corresponding buttons of the gas sensor.

19. The assembly according to claim 15, further comprising:
    an outlet filter disposed on an inner surface of the top cover at the outlet opening; and
    an inlet filter defined by the top cover at the inlet opening.

20. A method of assembling a device for use with a gas sensor, the method comprising:
    providing a buoyant housing configured to receive the gas sensor therein;
    defining an inlet opening in the housing;
    positioning a pump within the housing, wherein the pump is in fluid communication with:
       the inlet opening; and,
       the gas sensor in an instance in which the gas sensor is received by the housing, wherein the pump is configured to cause gas received by the inlet opening to be directed to the gas sensor for evaluation; and
    defining an outlet opening in the housing, wherein the outlet opening is configured to discharge gas exiting the gas sensor from the buoyant housing,
    wherein, in an operational condition in which the device is placed in a fluid, the buoyant housing is configured such that at least a portion of the buoyant housing floats above a surface of the fluid.

* * * * *